US011841348B2

(12) United States Patent
Li et al.

(10) Patent No.: US 11,841,348 B2
(45) Date of Patent: Dec. 12, 2023

(54) SYSTEM AND METHOD FOR EVALUATING THE EFFECT OF PROACTIVE UTILIZATION OF SPATIAL STRESS FIELD IN LABORATORY

(71) Applicant: CHINA UNIVERSITY OF PETROLEUM-BEIJING, Beijing (CN)

(72) Inventors: Caoxiong Li, Beijing (CN); Chenggang Xian, Beijing (CN); Yinghao Shen, Beijing (CN); Guoxin Li, Beijing (CN)

(73) Assignee: China University of Petroleum Beijing, Beijing (CN)

( * ) Notice: Subject to any disclaimer, the term of this patent is extended or adjusted under 35 U.S.C. 154(b) by 16 days.

(21) Appl. No.: 17/732,477

(22) Filed: Apr. 28, 2022

(65) Prior Publication Data

US 2023/0213423 A1 Jul. 6, 2023

(30) Foreign Application Priority Data

Dec. 30, 2021 (CN) .......................... 202111659090.1

(51) Int. Cl.
*G01N 3/12* (2006.01)
*G01N 15/08* (2006.01)

(52) U.S. Cl.
CPC ............. *G01N 3/12* (2013.01); *G01N 15/082* (2013.01); *G01N 2203/0019* (2013.01); *G01N 2203/0048* (2013.01); *G01N 2203/0066* (2013.01)

(58) Field of Classification Search
CPC .............. G01N 3/12; G01N 15/082; G01N 2203/0019; G01N 2203/0048; G01N 2203/0066; Y02E 10/10
USPC .......................................................... 73/783
See application file for complete search history.

(56) References Cited

U.S. PATENT DOCUMENTS

2017/0067337 A1* 3/2017 Havens .................. G01V 1/288

FOREIGN PATENT DOCUMENTS

| CN | 110500090 A | * | 11/2019 | ............. E21B 43/26 |
| CN | 111337648 A | * | 6/2020 | ............. G01N 33/24 |
| CN | 113514626 A | * | 10/2021 | |

* cited by examiner

*Primary Examiner* — Marrit Eyassu
(74) *Attorney, Agent, or Firm* — Ruggiero, McAllister & McMahon LLC

(57) ABSTRACT

A system and a method evaluate the effect of proactive utilization of a spatial stress field in laboratory. The system includes a rock sample placement device for placing a rock sample, a confining pressure control device for applying a set confining pressure to the rock sample, a fracture imaging device, a fracturing fluid injection device for injecting fracturing fluid into the perforation in the wellbore of the rock sample to form fractures within the rock sample, a stress measurement device, and a processing device for calculating a stress field proactive utilization coefficient of the rock sample.

10 Claims, 5 Drawing Sheets

SYSTEM AND METHOD FOR EVALUATING THE EFFECT OF PROACTIVE UTILIZATION OF SPATIAL STRESS FIELD IN LABORATORY

CROSS-REFERENCE TO RELATED APPLICATION

This application claims priority to Chinese Patent Application No. 202111659090.1, filed Dec. 30, 2021, which is hereby incorporated by reference in its entirety.

TECHNICAL FIELD

The present disclosure relates to the field of oil and gas field development engineering, and in particular to a system and a method for evaluating of the effect of proactive utilization of a spatial stress field in laboratory.

BACKGROUND

Tight oil and gas reservoirs are generally characterized by relatively low porosity and low permeability. During developing process, a large-scale hydraulic fracturing technology needs to be used to generate a large-scale artificial fracture network, so as to increase matrix conductivity, achieve the goal of improving resource utilization efficiency and recovery, and finally realize high-efficiency development. In the process of hydraulic fracturing, a large amount of fracturing fluid with proppant need to be injected into a rock formation in a short time, so as to change the stress field of the rock formation and cause rock fracture, and finally a connected fracture network is formed. At the same time, a large amount of injected fracturing fluid and proppant will generate induced stress around the fracture. When synchronous fracturing or zipper fracturing is used on multiple wells, the induced stresses field generated by each fracture will overlap each other to form a complex spatial stress field. But interwell interference is not negative for development all time. Under the condition of stereoscopic development, by setting multiple horizontal wells with staggered stacked laterals, the interwell introduced stress field can be used "from being passive to being proactive" to create complex fractures, so as to improve the resource utilization efficiency and recovery.

In the prior art, the field construction situation of the oil and gas field is mostly analyzed by artificial experience, to estimate the recovery of the field hydraulic fracturing construction scheme. However, the artificial experience can be used to only estimate the resource utilization efficiency and the recovery around the wellbore which has been hydraulically fractured, but not to evaluate the effect of proactive utilization of the introduced spatial stress field formed during the hydraulic fracturing process objectively and quantitatively.

There is an urgent need for a system and method for evaluating the effect of proactive utilization of a spatial stress field, especially in laboratory, so as to solve the problem that the resource utilization efficiency and recovery around the wellbore which has been hydraulically fractured in oil and gas field site can only be estimated by artificial experience, and the effect of proactive utilization of the spatial stress field formed during and after the hydraulic fracturing process cannot be estimated objectively and quantitatively.

SUMMARY

In order to solve the problem that the resource utilization efficiency and recovery around the wellbore which has been hydraulically fractured in oil and gas field site can only be estimated by artificial experience, and the effect of proactive utilization of the spatial stress field formed during and after the hydraulic fracturing process cannot be estimated objectively and quantitatively, embodiments of the present disclosure provide a system and a method for evaluation of the effect of proactive utilization of a spatial stress field in laboratory, which can establish a set of system of quantitative evaluation of the effect of proactive utilization of spatial stress field of stereoscopic well pattern equivalently under laboratory conditions, and can derive the optimal parameter combination of fracturing parameters, and extract main controlling factors by repeating the experiment under different fracturing parameters, and finally determined the fracturing scheme which can adequately use the spatial stress field in spatial stress field to create complex fracture network, so as to solve the problem that the resource utilization efficiency and recovery of the formation between the wellbores which have been hydraulically fractured in oil and gas field site can only be estimated by artificial experience, and the effect of proactive utilization of the spatial stress field formed in the hydraulic fracturing process cannot be estimated objectively and quantitatively in laboratory.

In order to solve the above technical problems, the specific technical scheme of the present disclosure is as follows:

In one aspect, an embodiment of the present disclosure provides a system for indoor evaluating the effect of proactive utilization of a spatial stress field in laboratory, comprising:

a rock sample placement device for placing a rock sample which is provided therein with a plurality of wellbores, the wellbore being provided with a plurality of perforations, the perforations in any adjacent two of the wellbores are staggered in horizontal and vertical directions of the rock sample;

a confining pressure control device for applying a set confining pressure to the rock sample in the rock sample placement device to simulate an original in-situ stress field of the rock sample in an actual formation;

a fracture imaging device for acquiring morphology and number of fractures inside the rock sample;

a fracturing fluid injection device connected to one end of the wellbore of the rock sample, for injecting fracturing fluid into the perforation in the wellbore of the rock sample to form fractures within the rock sample;

a stress measurement device for measuring the stress values inside the rock sample while injecting the fracturing fluid into the perforations of the wellbores by the fracturing fluid injection device;

a processing device for calculating a stress field proactive utilization coefficient of the rock sample based on morphology of the fracture, the number of the fractures, and the stress values, and for quantitatively evaluating the effect of proactive utilization of the spatial stress field according to the stress field proactive utilization coefficient and a preset proactive utilization coefficient threshold value.

In another aspect, the embodiments of the present disclosure further provide a method for evaluating the effect of proactive utilization of a spatial stress field by utilizing the system for evaluating the effect of proactive utilization of a spatial stress field in laboratory as described above, comprising:

placing the rock sample in the rock sample placement device;

applying a set confining pressure by the confining pressure control device to the rock sample in the rock sample placement device to form an original in-situ stress field of the rock sample in an actual formation;

injecting the fracturing fluid into perforations in the wellbores of the rock sample in the rock sample placement device by the fracturing fluid injection device in accordance with a fracturing scheme, such that the fractures is formed within the rock sample, and the fracturing scheme includes a start time at which the fracturing fluid is injected into each of the perforations and a flow curve over time for injecting the fracturing fluid into each of the perforations;

acquiring, by the fracture imaging device, morphology and number of fractures inside the rock sample;

measuring, by the stress measurement device, the stress values inside the rock sample;

calculating a stress field proactive utilization coefficient of the rock sample based on morphology of the fractures, the number of the fractures, and the stress values;

quantitatively evaluating the effect of proactive utilization of the spatial stress field according to the stress field proactive utilization coefficient and a preset proactive utilization coefficient threshold value.

In accordance with the embodiment herein, the rock sample is provided therein with a plurality of wellbores, the wellbore is provided with a plurality of perforations, the rock sample is placed inside the rock sample placement device, and then a set confining pressure is applied to the rock sample in the rock sample placement device by the confining pressure control device, to simulate an original in-situ stress field of the rock sample in an actual formation, then the fracturing fluid is injected into the perforations in the wellbore of the rock sample by the fracturing fluid injection device, to form a fracture in the rock sample, and morphology of fractures inside the rock sample is acquired by the fracture imaging device, and a stress value inside the rock sample is measured by the stress measurement device, and finally the processing device calculates a stress field proactive utilization coefficient of the rock sample based on morphology of the fracture, the number of the fractures, and the stress values inside the rock sample, and finally quantitatively evaluates the effect of proactive utilization of the spatial stress field according to the stress field proactive utilization coefficient and a preset proactive utilization coefficient threshold value. It is achievable to establish a set of system of quantitative evaluation of the effect of proactive utilization of spatial stress field of stereoscopic well pattern under laboratory conditions, and to repeat the experiment by changing fracturing parameters, and in which preferably the fracturing parameters are combined and main controlling factors are extracted to determine the fracturing scheme with the best effect of proactive utilization of the spatial stress field of the stereoscopic well pattern, so as to solve the problem that the recovery of the formation between the wellbores which have been hydraulically fractured in oil and gas field site can only be estimated by artificial experience, and the effect of proactive utilization of the spatial stress field formed in the hydraulic fracturing process cannot be estimated in laboratory objectively and quantitatively, and which can assist in optimizing the fracturing design parameters with better effect of proactive utilization of the spatial stress field of the stereoscopic well pattern, and provide support for the high-efficiency development of the tight reservoir.

BRIEF DESCRIPTION OF DRAWINGS

To illustrate more clearly the embodiments of the present disclosure or the technical schemes of the prior art, a brief description of the accompanying drawings in the embodiments or the prior art will be given below. Obviously, the accompanying drawings described below are only some embodiments described in the present disclosure. For those of ordinary skill in the art, other drawings can also be obtained without any creative labor from these drawings.

DETAILED DESCRIPTION

Hereinafter the technical solution in the embodiments of the present disclosure will be described clearly and integrally in combination with the accompanying drawings in the embodiments of the present disclosure, and obviously the described embodiments are merely part of the embodiments, not all of the embodiments. Any other embodiment obtained by those skilled in the art based on the embodiments of the present disclosure without paying any creative labor fall within the protection scope of the present disclosure.

It should be noted that the terms "first," "second" and the like in the description and claims herein and in the above-mentioned drawings are used to distinguish between similar objects and are not necessarily used to describe a particular order or precedence. It should be understood that the data so used may be interchanged where appropriate so that the embodiments described herein can be implemented in an order other than those illustrated or described herein. Furthermore, the terms "comprising" and "having" and any variations thereof are intended to cover non-exclusive inclusions, such as, for example, a process, a method, an apparatus, a product or a device comprising a series of steps or units need not to be limited to those steps or units that are clearly listed, but may include other steps or units that are not explicitly listed or inherent to these processes, methods, products or devices.

Figure 1:
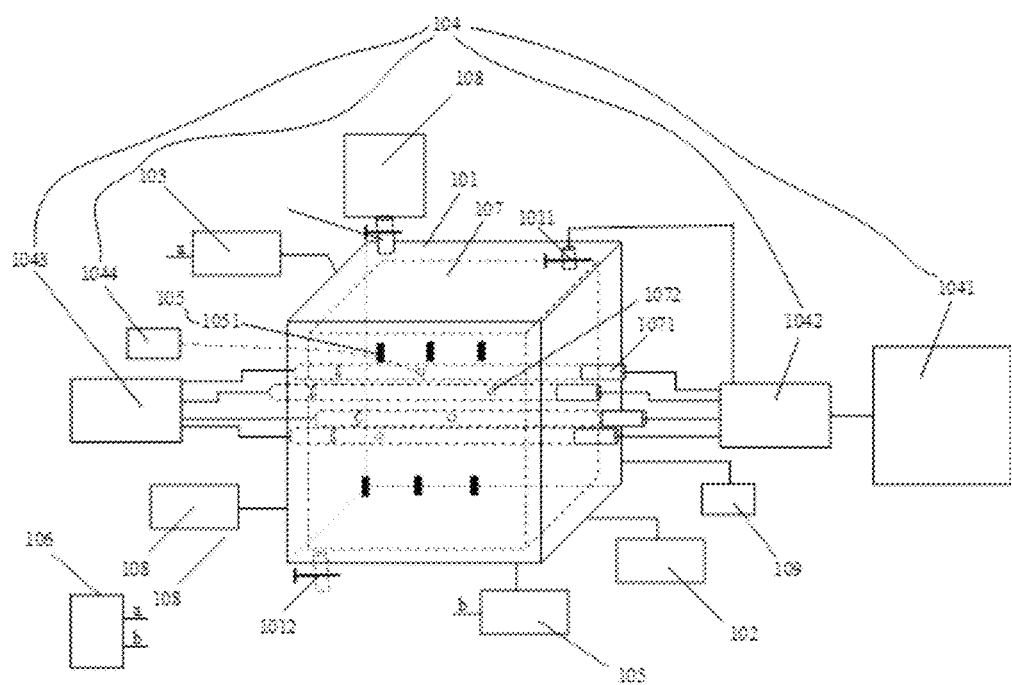
FIG. 1 is a structural schematic diagram of a system for evaluating the effect of proactive utilization of a spatial stress field in laboratory according to an embodiment of the present disclosure.

FIG. 1 is a structural schematic diagram of a system for evaluating the effect of proactive utilization of a spatial stress field in laboratory according to an embodiment of the present disclosure, comprising a rock sample placement device 101, a confining pressure control device 102, a fracture imaging device 103, a fracturing fluid injection device 104, a stress measurement device 105 and a processing device 106, and specifically, the rock sample placement device 101 is used for placing a rock sample 107 which is provided therein with a plurality of wellbores 1071, the wellbore 1071 being provided with a plurality of perforations 1072, the perforations 1072 in any adjacent two of the wellbores 1071 are staggered in horizontal and vertical directions of the rock sample;

the confining pressure control device 102 is used for applying a set confining pressure to the rock sample 107 in the rock sample placement device 101 to form an original in-situ stress field of the rock sample 107 in an actual formation;

the fracture imaging device 103 is used for acquiring morphology and number of fractures inside the rock sample 107;

the fracturing fluid injection device 104 is connected to one end of the wellbore 1071 of the rock sample 107, for injecting fracturing fluid into the perforation 1072 in the wellbore 1071 of the rock sample 107 to form a fracture within the rock sample 107;

the stress measurement device 105 is used for measuring a stress value inside the rock sample 107 while injecting the fracturing fluid into the perforations 1072 of the wellbore 1071;

the processing device 106 is used for calculating a stress field proactive utilization coefficient of the rock sample 107 based on morphology of the fracture, the number of the fractures, and the stress values, and for quantitatively evaluating the effect of proactive utilization of the spatial stress field according to the stress field proactive utilization coefficient and a preset proactive utilization coefficient threshold value.

With the system for evaluating the effect of proactive utilization of a spatial stress field in laboratory provided in the embodiment of the present disclosure, the rock sample 107 is provided therein with a plurality of wellbores 1071, the wellbore 1071 is provided with a plurality of perforations 1072, the rock sample 107 is placed inside the rock sample placement device 101, and then a set confining pressure is applied to the rock sample 107 in the rock sample placement device 101 by the confining pressure control device 102, to simulate an original in-situ stress field of the rock sample 107 in an actual formation, then the fracturing fluid is injected into the perforations 1072 in the wellbore 1071 of the rock sample 107 by the fracturing fluid injection device 104, to form a fracture in the rock sample 107, and morphology of fractures inside the rock sample 107 is acquired by the fracture imaging device 103, and a stress value inside the rock sample 107 is measured by the stress measurement device 105, and finally the processing device 106 calculates a stress field proactive utilization coefficient of the rock sample 107 based on morphology of the fracture, the number of the fractures, and the stress values inside the rock sample 107, and finally quantitatively evaluates the effect of proactive utilization of the spatial stress field according to the stress field proactive utilization coefficient and a preset proactive utilization coefficient threshold value. It is achievable to establish a set of system of quantitative evaluation of the effect of proactive utilization of spatial stress field of stereoscopic well pattern under laboratory conditions, and to repeat the experiment by changing fracturing parameters, and in which preferably the fracturing parameters are combined and main controlling factors are extracted to determine the fracturing scheme with the best effect of proactive utilization of the spatial stress field of the stereoscopic well pattern, so as to solve the problem that the recovery of the formation between the wellbores which have been hydraulically fractured in oil and gas field site can only be estimated by artificial experience, and the effect of proactive utilization of the spatial stress field formed in the hydraulic fracturing process cannot be estimated in laboratory objectively and quantitatively, and which can assist in optimizing the fracturing design parameters with better effect of proactive utilization of the spatial stress field of the stereoscopic well pattern, and provide support for the high-efficiency development of the tight reservoir.

In the embodiments of the present disclosure, the rock sample 107 may be cube in shape, made from field outcrops, artificial cores, or downhole cores, and placed inside the rock sample placement device 101. The interior of the rock sample placement device 101 is a closed cavity. Preferably, the shape of an internal closed cavity of the rock sample placement device 101 is a cube, and the confining pressure control device 102 can load a true triaxial stress to the rock sample 107. The fracture imaging device 103 may scan and image the distribution of internal fractures of the rock sample 107. Specifically, the fracture imaging device 103 can scan the interior of the rock sample 107 by three-dimensional computed tomography (3D-CT), acoustic emission source localization, or the like.

It should be noted that the wellbore 1071 discussed in the system in this document indicates the equivalent wellbore or wellbore model, not the real wellbore in drilling field.

Figure 2:
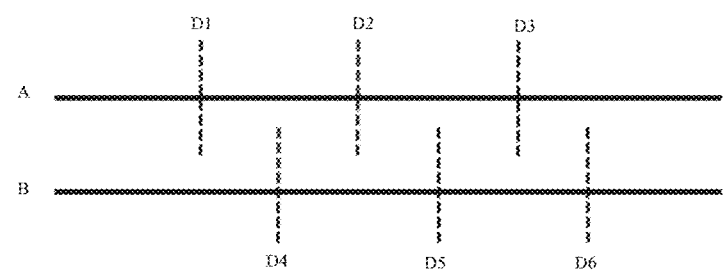
FIG. 2 is a structural schematic diagram showing that the perforations in any two adjacent wellbores in the same rock sample are staggered in the horizontal and vertical directions of the rock sample according to an embodiment of the present disclosure.

In addition, the perforations 1072 are provided inside the wellbore 1071 in the rock sample 107. The wellbores 1071 penetrate through the rock sample 107 in parallel and horizontally, in a structure of a single layer, two or more layers, in which two vertically adjacent layers are staggered. The perforations 1072 in any two adjacent wellbores 1071 in the same sample 107 are staggered in the horizontal and vertical directions of the rock sample 107. Illustratively, the staggered placement may be as shown in FIG. 2. In FIG. 2, A and B represent two adjacent wellbores in the same rock sample, the direction parallel to the wellbore A and the wellbore B is the horizontal direction of the rock sample and the direction perpendicular thereto is the vertical direction of the rock sample. In FIGS. 2, D1, D2 and D3 are the locations of the three perforations in the wellbore A, and D4, D5 and D6 are the locations of three perforations in the wellbore B. As can be seen from FIG. 2, the locations D1, D2 and D3 of the perforations in the wellbore A and the locations D4, D5 and D6 of the perforations in the wellbore B are staggered in the horizontal and vertical directions.

When the fracturing fluid is injected into the perforations 1072 in the wellbore 1071 of the rock sample 107 by the fracturing fluid injection device 104, a complex fracture network may be formed within the rock sample 107, wherein the fracturing fluid may be deionized water, formation water, fracturing fluid, or the like. The stress measurement device 105 measures the stress values inside the rock sample 107 at each point in time while injecting the fracturing fluid into the perforations 1072 by the fracturing fluid injection device 104. The fracture imaging device 103 images the fractures inside the rock sample 107, and obtains the morphology and the number of the fractures. The processing device 106 calculates a stress field proactive utilization coefficient of the rock sample 107 based on the morphology and the number of the fractures obtained by the fracture imaging device 103, and the stress values obtained by the stress measurement device 105. The stress field proactive utilization coefficient is an important parameter for quantitative evaluation of the effect of proactive utilization of spatial stress field of stereoscopic well pattern. When the influence of other fractures induced stresses is greater, the number of the fractures is greater, the area of fracture network potential area is larger, and the stress field proactive utilization coefficient is larger. The proactive utilization coefficient threshold value can be determined according to the fracturing condition and production efficiency of a single well in the formation where the rock sample 107 is located. Alternatively, the final recoverable reserves of a single well are determined firstly according to the economic production indexes, the spatial stress field of the adjacent wells is calculated by capturing the fracturing conditions of the adjacent wells in the formation, and the stress field proactive utilization coefficient is calculated based on the spatial stress field, and finally the proactive utilization coefficient threshold value is determined according to the stress field proactive utilization coefficient and the final recoverable reserves of the single well. When the stress field proactive utilization coefficient is larger than the preset proactive utilization coefficient threshold value, it indicates that the effect of proactive utilization of the spatial stress field has reached the requirement.

According to an embodiment of the present disclosure, in order to evaluate the effect of proactive utilization of the stress field of different fracturing schemes, continuously as shown in FIG. 1, the perforation 1072 is provided with a valve (not shown), and the fracturing fluid injection device 104 further comprises a fracturing fluid injection pump 1041, a flow switching control unit 1042, a wellbore pressure balancing unit 1043, and a flow injection control unit 1044.

The fracturing fluid injection pump 1041 is connected to a first end of the flow switching control unit 1042; a second end of the flow switching control unit 1042 is connected to head ends of all of the wellbores 1071 of the rock sample 107; and tail ends of all of the wellbores 1071 of the rock sample 107 are connected to the wellbore pressure balancing unit 1043.

The fracturing fluid injection pump 1041 is used to inject the fracturing fluid into the head ends of all of the wellbores 1071 of the rock sample 107 in a predetermined order though the control of the flow switching control unit 1042.

The flow switching control unit 1042 is used to control the flow rate of the fracturing fluid, the sequence of injection of the fracturing fluid injected into the wellbore 1071 of the rock sample 107.

The flow injection control unit 1044 is used to control opening or closing of the valve on the perforation 1072, thereby controlling the sequence of injection of the fracturing fluid injected into the perforation 1072 of the wellbore 1071.

The wellbore pressure balancing unit 1043 is used to control communication of the tail ends of the wellbores 1071 of the rock sample 107 so as to balance the pressure inside the wellbores 1071 of the rock sample 107.

In the embodiment of the present disclosure, the flow switching control unit 1042 injects the fracturing fluid into the wellbore 1071 of the rock sample 107 through the fracturing fluid injection pump 1041. The flow switching control unit 1042 can switch the fracturing fluid injected into each wellbore 1071 in real time, control the flow rate and pressure in each wellbore 1071, and the flow injection control unit 1044 may control the sequence of injection of the fracturing fluid injected into the perforation 1072 of the wellbore 1071. For example, a valve is provided on each perforation 1072. The flow injection control unit 1044 may control the respective valves to be opened or closed so that the fracturing fluid in the wellbore 1071 is injected into the respective perforations 1072, enabling simulation of synchronous fracturing, zipper fracturing, or simple fracturing. The wellbore pressure balancing unit 1043 can control communication of the tail ends of the wellbores 1071. When a plurality of wellbores 1071 are synchronously fractured, the tail portions of the synchronously fractured wellbores 1071 are communicated to achieve equalization of the pressure inside the synchronously fractured wellbores 1071. When any two or more wellbores 1071 are engaged in other fracturing schemes than the synchronous fracturing, communication of the tail portions of the corresponding wellbore 1071 is closed.

In particular, when simulating synchronous fracturing, the wellbore pressure balancing unit 1043 controls the tail valves of all of the synchronously fractured wellbores 1071 to be opened and communicate with one another, to balance the pressure inside the wellbores 1071. The flow switching control unit 1042 and the flow injection control unit 1044 control the fracturing fluid to be simultaneously injected into the perforations 1072 of different wellbores 1071 for fracturing. That is, the fracturing fluid is simultaneously injected into the perforations 1072 of the wellbores 1071 in a far-to-near order of distances from the perforations 1072 to the flow switching control unit 1042. Illustratively, continuously as shown in FIG. 2, right ends of the wellbore A and the wellbore B are connected to the flow switching control unit 1042, and left ends of the wellbore A and the wellbore B are connected to the wellbore pressure balancing unit 1043. Therefore, when simulating synchronous fracturing, the sequence of fracturing fluid injection is D1+D4, D2+D5, D3+D6, wherein "+" indicates that the fracturing fluid is injected into two perforations simultaneously.

When simulating the zipper fracturing, the wellbore pressure balancing unit 1043 controls the tail valves of all of the synchronously fractured wellbores 1071 to be closed, so that the wellbores 1071 are not in communication with each other. The flow switching control unit 1042 and the flow injection control unit 1044 control the fracturing fluid to be injected into different perforations 1072 of different wellbores 1071 respectively, for fracturing. That is, firstly, the fracturing fluid is injected into the perforation in a certain wellbore that the perforation is farthest from the flow switching control unit 1042, then the fracturing fluid is injected into the perforation in another wellbore that the perforation is farthest from the flow switching control unit 1042. After completion of injecting the fracturing fluid into the perforations of all wellbores that the perforations are farthest from the flow switching control unit 1042, the process goes back to the wellbore where the fracturing fluid is injected at first, the fracturing fluid is injected into the perforation of the wellbore that the perforation is second-farthest from the flow switching control unit 1042, and so forth, until the fracturing fluid is injected into all the perforations in all the wellbores. Illustratively, continuously as shown in FIG. 2, when simulating the zipper fracturing, the sequence of fracturing fluid injection is D1, D4, D2, D5, D3, and D6.

When simulating the simple fracturing, the wellbore pressure balancing unit 1043 controls the tail valves of all of the synchronously fractured wellbores 1071 to be closed, so that the wellbores 1071 are not in communication with each other. The flow switching control unit 1042 and the flow injection control unit 1044 control the fracturing fluid to be injected into different perforations 1072 of different wellbores 1071 respectively, for fracturing. That is, the fracturing fluid is injected into the plurality of perforations of the wellbore sequentially in a far-to-near order of distances from the perforations to the fracturing fluid injection device 104. After completion of injecting the fracturing fluid into all of the perforations of the wellbore, repeating the above described step in another wellbore, until the fracturing fluid is injected into all the perforations in all the wellbores. Illustratively, continuously as shown in FIG. 2, when simulating the simple fracturing, the sequence of fracturing fluid injection is D1, D2, D3, D4, D5 and D6.

According to an embodiment of the present disclosure, in order to obtain more accurate stress values, the stress measurement device 105 further comprises a plurality of stress sensors 1051 disposed inside the rock sample.

The stress sensor 1051 is used to measure stress values at individual points within the rock sample 107.

According to an embodiment of the present disclosure, in order to further simulate liquid saturation of the actual formation, so as to cause the effect of proactive utilization of the stress field evaluated in the laboratory to be closer to the actual engineering site, the rock sample placement device 101 further includes a water injection valve 1011 and a water discharge valve 1012, and the water injection valve 1011 is connected to the fracturing fluid injection device 104.

The fracturing fluid injection device 104 is further used to inject the fracturing fluid into interior of the rock sample placement device 101 through the water injection valve 1011, so as to soak the rock sample 107 in the fracturing liquid.

The water discharge valve 1012 is used to discharge the fracturing fluid from the interior of the rock sample placement device 101.

In the embodiment of the present disclosure, the fracturing fluid injection device 104 may inject the fracturing fluid into the rock sample placement device 101 through a water injection valve 1011, for producing the saturation of the rock sample 107 such that the saturation of the rock sample 107 is closer to that of the actual formation. Specifically, the rock sample 107 may firstly be placed in the rock sample placement device 101, and the water injection valve 1011 and the water discharge valve 1012 may be opened. The fracturing fluid injection device 104 injects the fracturing fluid into the rock sample placement device 101 through the water injection valve 1011, then fracturing fluid is discharged from the water discharge valve 1012 to remove impurities and rock debris within the rock sample 107, thereby improving calculation accuracy. When the liquid discharged by the water discharge valve 1012 does not contain impurities and/or rock debris, the water discharge valve 1012 is closed. When the level of the fracturing fluid is above the upper surface of the rock sample 107, the fracturing fluid injection device 104 is stopped from injecting the fracturing fluid into the rock sample placement device 101, and the water injection valve 1011 is closed to saturate the rock sample 107.

It should be noted that the fracturing fluid may also be injected into the rock sample placement device 101 by another liquid injection device, and the embodiment of this specification is not limited thereto.

According to an embodiment of the present disclosure, in order to accelerate the saturation of the rock sample 107, the system for evaluating the effect of proactive utilization of a spatial stress field in laboratory provided in the embodiment of the present disclosure further comprises a vacuum pump 108, and the rock sample placement device 101 further includes a vacuum pump valve 1013.

The vacuum pump 108 is located outside the rock sample placement device 101 and is connected to the vacuum pump valve 1013 of the rock sample placement device 101.

The vacuum pump 108 is used to pump gas from the interior of the rock sample placement device 101 through the vacuum pump valve 1013 after the fluid level of the fracturing fluid is above an upper surface of the rock sample.

In the embodiment of the present disclosure, the interior space of the rock sample placement device 101 is closed. When the air in the rock sample placement device 101 is evacuated by the vacuum pump 108, the gas above the level of the fracturing fluid is reduced in pressure by being evacuated. Since the compressibility of the fracturing fluid is low and the pressure of the gas-solid bulk coefficient inside the rock sample placement device 101 is reduced, the drop in gas pressure above the liquid level will be transferred to the space inside of the rock sample 107, such that the gas in the interior of the rock sample 107 is expanded in volume so as to come out of the surface of the rock sample 107, at the same time, the gas is moved upward by buoyancy until it is exposed out of the liquid surface, and is evacuated by the vacuum pump 108 out of the cavity of the rock sample placement device 101, and after a period of time, the vacuum pump 108 is closed to restore the normal pressure, the gas pressure inside the rock sample 107 is restored to normal pressure, and the volume is contracted. The shrunk volume of the gas enables the fracturing fluid to enter the deeper pores of the rock sample 107, thus accelerating the saturation speed of the rock sample 107 as a whole and shortening the experimental time for the saturation of the rock sample 107. In the above process, there is an effect of spontaneous imbibition between the rock sample 107 and the fracturing fluid. Upon entry of the fracturing fluid into deeper pores inside the core sample 107, the fracturing fluid is able to spontaneously enter into the finer internal pores of the rock sample 107 under the combined influence of capillary forces and the water-absorbing clay minerals in the rock sample 107. The saturation speed of the rock sample 107 is also accelerated macroscopically.

According to an embodiment of the present disclosure, in order to further simulate the temperature of the actual formation, so as to cause the effect of proactive utilization of the stress field evaluated in the laboratory to be closer to the actual engineering site, the system for evaluating the effect of proactive utilization of a spatial stress field in laboratory provided in the embodiment of the present disclosure further comprises a temperature control device 109.

The temperature control device 109 is used for regulating temperature inside the rock sample placement device 101.

In the embodiment of the present disclosure, the temperature control device 109 may bring the temperature of the rock sample 107 within the rock sample placement device 101 to be closer to the actual formation, thereby improving the calculation accuracy.

It should be noted that the above described system can also be used for experiments under the conditions of different saturations/different temperatures/different injection rates/different confining pressures/different immersion times of rock samples, and the other parameters are the same, to obtain the final spatial fracture morphology and spatial stress field distribution of each experiment, so that the influence on the stress field proactive utilization coefficient by different parameters can be obtained, and the embodiment of this specification is not limited.

It should be noted that, when evaluating the effect of proactive utilization of the stress field of dry rock samples, the process of injecting the fracturing fluid into the rock sample placement device 101 through the water injection valve 1011 and accelerating the saturation of the rock sample 107 by the vacuum pump 108 may be omitted.

Figure 3:
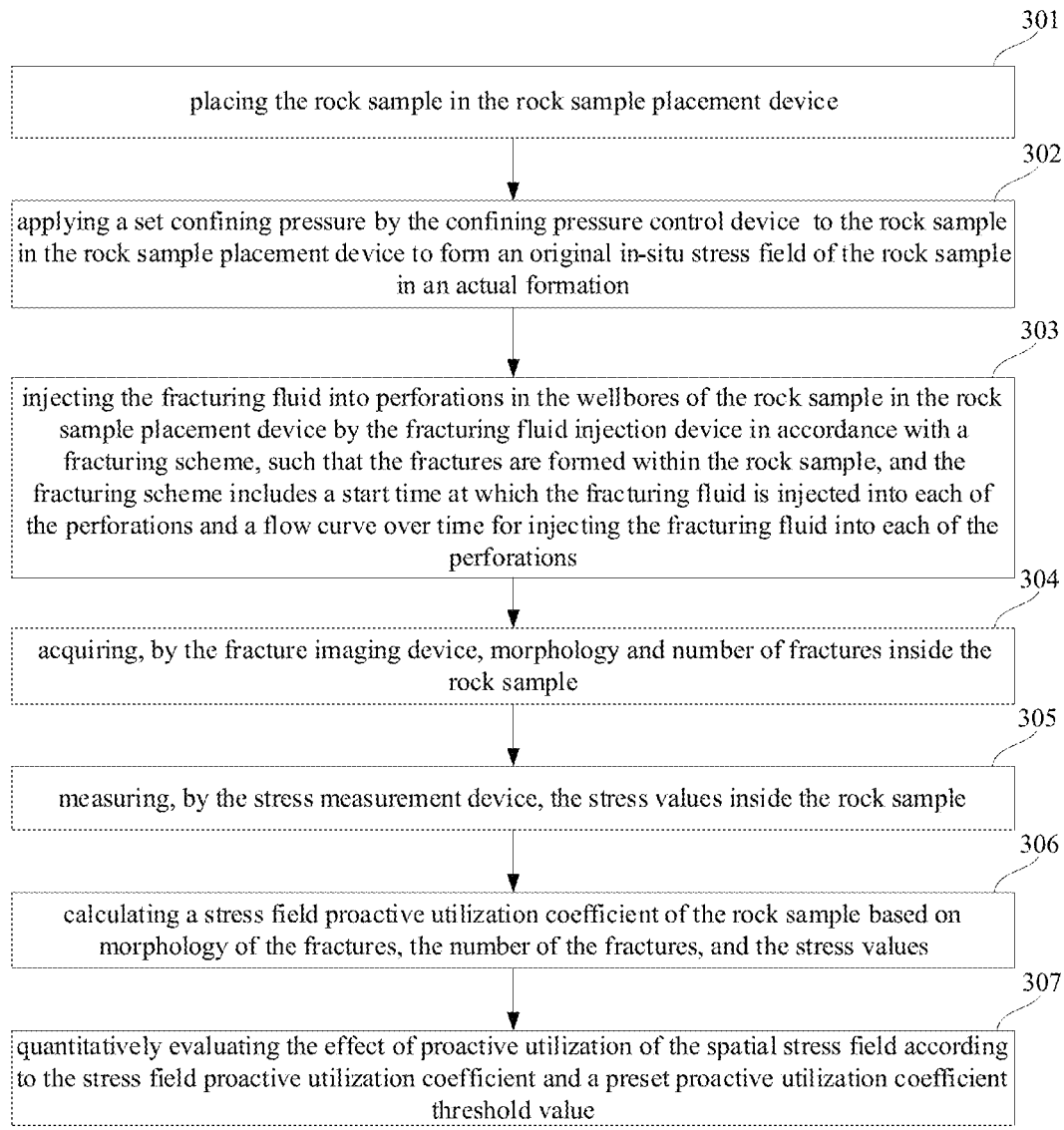
FIG. 3 is a flow chart of a method for evaluating the effect of proactive utilization of a spatial stress field in laboratory according to an embodiment of the present disclosure.

Based on the same inventive concept, the embodiment of the present disclosure further provides a method for evaluating the effect of proactive utilization of a spatial stress field in laboratory that utilizes the system for evaluating the effect of proactive utilization of a spatial stress field in laboratory as shown in FIG. 1, so as to evaluate the effect of proactive utilization of spatial stress field of stereoscopic well pattern under laboratory conditions. FIG. 3 is a flow chart of a method for evaluating the effect of proactive utilization of a spatial stress field in laboratory according to an embodiment of the present disclosure. The process of quantitative evaluation of the effect of proactive utilization of a spatial stress field under laboratory conditions is described in FIG. 3, but more or fewer operating steps may be included based on routine or non-creative work. The order of the steps listed in the embodiments is merely one of various execution orders of the steps, rather than a unique execution order. When being executed at an actual system or device product, the steps may be performed in sequence or in parallel according to the methods illustrated in the embodiments or drawings. Specifically, as shown in FIG. 3, the method may comprise:

a step 301: placing the rock sample in the rock sample placement device;

a step 302: applying a set confining pressure by the confining pressure control device to the rock sample in the rock sample placement device to form an original in-situ stress field of the rock sample in an actual formation;

a step 303: injecting the fracturing fluid into perforations in the wellbores of the rock sample in the rock sample placement device by the fracturing fluid injection device in accordance with a fracturing scheme, such that the fractures are formed within the rock sample, and the fracturing scheme includes a start time at which the fracturing fluid is injected into each of the perforations and a flow curve over time for injecting the fracturing fluid into each of the perforations;

a step 304: acquiring, by the fracture imaging device, morphology and number of fractures inside the rock sample;

a step 305: measuring, by the stress measurement device, the stress values inside the rock sample;

a step 306: calculating a stress field proactive utilization coefficient of the rock sample based on morphology of the fractures, the number of the fractures, and the stress values;

a step 307: quantitatively evaluating the effect of proactive utilization of the spatial stress field according to the stress field proactive utilization coefficient and a preset proactive utilization coefficient threshold value.

By the method for evaluating the effect of proactive utilization of a spatial stress field in laboratory described in the embodiment of the present disclosure, quantitative evaluation of the effect of proactive utilization of spatial stress field of stereoscopic well pattern is realized under the laboratory condition.

According to an embodiment of the present disclosure, the fracture morphology further comprises a fracture area and a tortuosity of the fractures.

A formula for calculating a stress field proactive utilization coefficient of the rock sample based on the morphology of the fractures and the stress values can be shown as in the following (1)

$$Q_j = \frac{\frac{n_j}{\overline{\sigma}_j}\sum_{i=1}^{n_j} S_{i,j}\tau_{i,j}\sin\overline{\theta}_{i,j}}{\frac{n_1}{\overline{\sigma}_1}\sum_{i=1}^{n_1} S_{i,1}\tau_{i,1}\sin\overline{\theta}_{i,1}} \quad (1)$$

wherein, $Q_j$ represents the stress field proactive utilization coefficient, which is calculated by the j-th experiment using an experimental method for evaluating the effect of proactive utilization of the spatial stress field in laboratory, $n_j$ represents the number of fractures created on the rock sample through the j experiments, $\overline{\sigma}_j$ represents an average value of the stress values obtained by measurement at a plurality of positions inside the rock sample by the stress measurement device after completion of the j-th experiment, $S_{i,j}$ represents the fracture area of the i-th fracture among the fractures generated in the rock sample after completion of the j-th experiment, $\tau_{i,j}$ represents the tortuosity of the i-th fracture among the fractures generated in the rock sample after completion of the j-th experiment, $\overline{\theta}_{i,j}$ represents an average angle between a fracture surface of the i-th fracture and the direction of the maximum horizontal principal stress of the original in-situ stress field, in the fractures generated in the rock sample after completion of the j-th experiment, j=1 represents a background experiment carried by the experimental method for evaluating the effect of proactive utilization of the spatial stress field in laboratory.

The background experiment comprises:

a step S1: injecting, by the fracturing fluid injection device, the fracturing fluid into the plurality of perforations of the wellbore of the rock sample sequentially in a far-to-near order of distances from the perforations to the fracturing fluid injection device, according to the fracturing scheme of the background experiment;

a step S2: after completion of injection of the fracturing fluid into all of the perforations of the wellbore, repeating the step S1 in another wellbore until all perforations of all wellbores of the rock sample complete injection of the fracturing fluid to obtain the number $n_1$ of the fractures generated on the rock sample, the an average value $\overline{\sigma}_1$ of the stress values at the plurality of locations inside the rock sample, the fracture area $S_{i,1}$ and the tortuosity $\tau_{i,1}$ of the fractures inside the rock sample, and the average angle $\overline{\theta}_{i,1}$ between the fracture surface of the fracture inside the rock sample and the direction of the maximum horizontal principal stress of the original in-situ stress field, in the background experiment.

In the embodiment of the present disclosure, the original in-situ stress field may be derived directly by the confining pressure control device 102. The number of the fractures, the fracture area of each fracture, the tortuosity, and the average angle between the fracture surface and the direction of the maximum horizontal principal stress of the original in-situ stress field can be obtained directly from the data of fracture morphology in the rock sample 107 at the final time recorded by the fracture imaging device 103. The stress values at a plurality of locations inside the rock sample 107 can be obtained from the measurement results of the stress sensor 1051.

Figure 4:
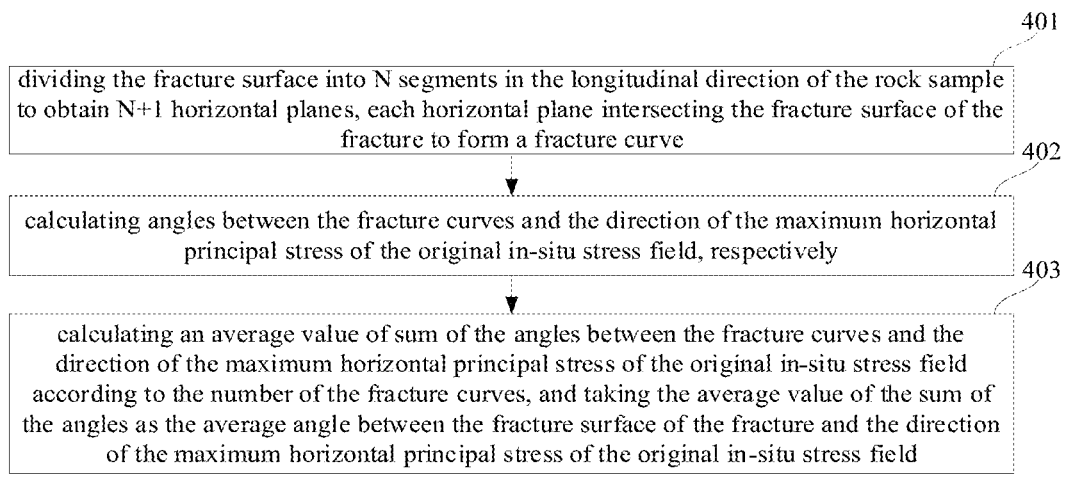
FIG. 4 shows a process of calculating the average angle between the fracture surface of the fractures and the direction of the maximum horizontal principal stress of the original in-situ stress field according to an embodiment of the present disclosure.

According to an embodiment of the present disclosure, as shown in FIG. 4, the step of calculating the average angle between the fracture surface of the fracture and the direction of the maximum horizontal principal stress of the original in-situ stress field, includes:

a step 401: dividing the fracture surface into N segments in the longitudinal direction of the rock sample to obtain N+1 horizontal planes, each horizontal plane intersecting the fracture surface of the fracture to form a fracture curve;

a step 402: calculating angles between the fracture curves and the direction of the maximum horizontal principal stress of the original in-situ stress field, respectively;

a step 403: calculating an average value of sum of the angles between the fracture curves and the direction of the maximum horizontal principal stress of the original in-situ stress field according to the number of the fracture curves, and taking the average value of the sum of the angles as the average angle between the fracture surface of the fracture and the direction of the maximum horizontal principal stress of the original in-situ stress field.

According to an embodiment of the present disclosure, the step of calculating angles between the fracture curves and the direction of the maximum horizontal principal stress of the original in-situ stress field, includes:

through the formula (2), $$\bar{\theta} = \int_L \frac{1}{\rho(\theta)} ds = \int_{\theta\_start}^{\theta\_end} \frac{\sqrt{\rho^2(\theta) + \rho'^2(\theta)}}{\rho(\theta)} d\theta \qquad (2)$$

calculating the angle between the fracture curve and the direction of the maximum horizontal principal stress of the original in-situ stress field in a polar coordinate system of the fracture curve, wherein $\bar{\theta}$ represents the angle between the fracture curve and the direction of the maximum horizontal principal stress of the original in-situ stress field, L represents the length of the fracture curve, $\rho(\theta)$ represents a representation of the path of the fracture curve in the polar coordinate system, $\theta$ represents the angular coordinate of any point on the path of the fracture curve in the polar coordinate system, $$\int_L \frac{1}{\rho(\theta)} ds$$

represents the integration of the function $\rho(\theta)$ over the length of the fracture curve along the arc length derivative ds-curve, $$\rho'(\theta) = \frac{d\rho(\theta)}{d\theta}$$

and θ_start, θ_end represent the angular coordinates of a starting point and an ending point of the path of the fracture curve in the polar coordinate system, respectively; or, through the formula (3), $$\bar{\theta} = \int_L f(s) ds = \int_{x\_start}^{x\_end} \frac{\sqrt{1 + f'^2(x)}}{\sqrt{x^2 + f^2(x)}} dx \qquad (3)$$

calculating the angle between the fracture curve and the direction of the maximum horizontal principal stress of the original in-situ stress field in a plane rectangular coordinate system of the fracture curve, wherein $\bar{\theta}$ represents the angle between the fracture curve and the direction of the maximum horizontal principal stress of the original in-situ stress field, L represents the length of the fracture curve, $f(x)$ represents a representation of the path of the fracture curve in the plane rectangular coordinate system, x represents the abscissa of any point on the path of the fracture curve in the plane rectangular coordinate system, $\int_L f(s) ds$ represents the integration of the function $f(x)$ over the length of the fracture curve along the arc length derivative ds-curve, $$f'(x) = \frac{df(x)}{dx}$$

and x_start, x_end represent the abscissa of a starting point and an ending point of the path of the fracture curve in the plane rectangular coordinate system, respectively;

any point on the path of the fracture curve satisfies the formula (4)

$$\tan\theta_{uni} = f'(x) = \frac{\rho(\theta)\cos\theta + \rho'(\theta)\sin\theta}{-\rho(\theta)\sin\theta + \rho'(\theta)\cos\theta} \qquad (4)$$

wherein $\theta_{uni}$ represents the direction of the maximum horizontal principal stress at a certain point on the path of the fracture curve.

In the embodiment of the present disclosure, the direction $\theta_{uni}$ of the maximum horizontal principal stress at a certain point on the path of the fracture curve can be obtained directly by the true triaxial stress loaded on the rock sample 107 by the confining pressure control device 102 of the system for evaluating the effect of proactive utilization of a spatial stress field in laboratory provided by the embodiment of this specification.

Figure 5:
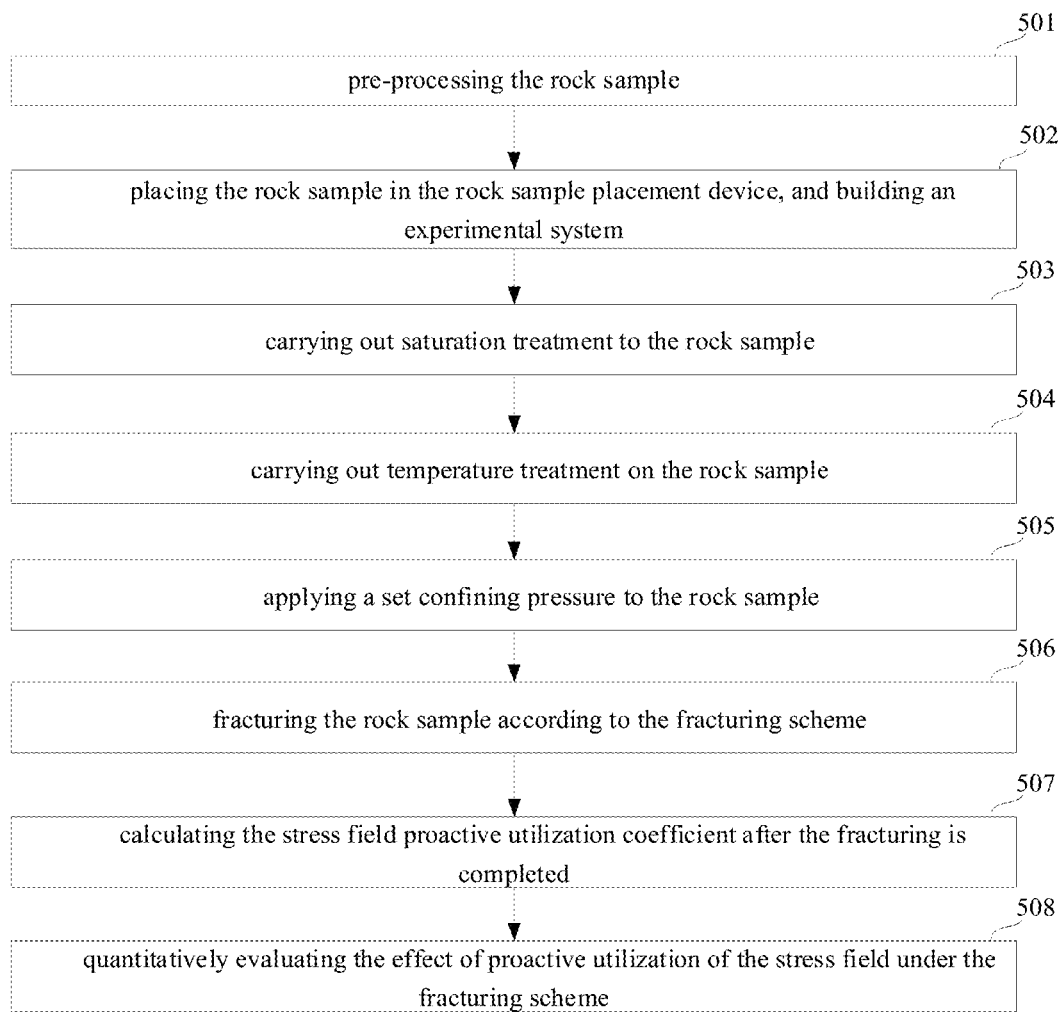
FIG. 5 is a flow schematic diagram of a method for evaluating the effect of proactive utilization of a spatial stress field in laboratory according to an embodiment of the present disclosure.

FIG. 5 is a flow schematic diagram of a method for evaluating the effect of proactive utilization of a spatial stress field in laboratory that utilizes the system for evaluating the effect of proactive utilization of a spatial stress field in laboratory as shown in FIG. 1 according to an embodiment of the present disclosure, and describes the steps for evaluating the effect of proactive utilization of a spatial stress field by utilizing the system for evaluating the effect of proactive utilization of a spatial stress field in laboratory as shown in FIG. 1. It should be noted that the steps and sequences described in this figure are not the only steps and sequences of evaluating the effect of proactive utilization of a spatial stress field in laboratory according to the embodiment of the present disclosure. For those skilled in the art, the steps and sequences of other evaluating the effect of proactive utilization of a spatial stress field in laboratory can also be obtained according to the contents described in the figure, and the embodiment of the present specification is not limited.

Specifically, the steps for evaluating the effect of proactive utilization of a spatial stress field include:

a step 501: pre-processing the rock sample;

this step specifically includes sampling at least two rock samples, processing the rock samples into cubes of the same size, and deploying a plurality of wellbores inside the rock sample, and deploying a plurality of horizontally and vertically staggered perforations within the wellbore, wherein the number of the wellbores, the positions of the wellbores, the number of the perforations, and the positions of the perforations, of different rock samples are respectively all the same.

A step 502: placing the rock sample in the rock sample placement device, and building an experimental system;

this step specifically includes placing the rock samples respectively in the rock sample placement device, connecting the fracturing fluid injection pump to the first end of the flow switching control unit, connecting the second end of the flow switching control unit to the head ends of all of the wellbores in the rock sample, connecting the tail ends of all of the wellbores of the rock sample to the wellbore pressure balancing unit, and connecting the flow injection control unit to the valves on the perforations.

A step 503: carrying out saturation treatment to the rock sample;

this step specifically includes opening the water injection valve and the water discharge valve on the rock sample placement device, and injecting the fracturing fluid into the rock sample placement device through the fracturing fluid injection device and the water injection valve, and immersing the rock sample in the liquid, wherein when the fracturing fluid discharged by the water discharge valve does not contain impurities and/or rock debris, the water discharge valve is closed; when the level of the fracturing fluid is above the upper surface of the rock sample, the fracturing fluid injection device is stopped from injecting the fracturing fluid into the rock sample placement device, and the water injection valve is closed; opening the vacuum pump valve, and evacuating the air in the rock sample placement device by the vacuum pump, to accelerate the saturation of the rock sample and to cause the saturation to be the same as the saturation of the actual target formation. It should be noted that the step 503 should be skipped when evaluating the effect of proactive utilization of the stress field for dry rock samples.

A step 504: carrying out temperature treatment on the rock sample;

In this step, the temperature of the rock sample is controlled by the temperature control device to be the same as the temperature of the actual target formation.

A step 505: applying a set confining pressure to the rock sample;

In this step, the set confining pressure is applied to the rock sample by the confining pressure control device, so that the original in-situ stress field of the rock sample is the same as that of the actual target formation.

A step 506: fracturing the rock sample according to the fracturing scheme;

In this step, the background experiment described in the embodiment of the present specification is performed on one of the rock samples at first, to obtain the number of the fractures generated on the rock sample, the an average value of the stress values at the plurality of locations inside the rock sample, the fracture areas and the tortuosity of the fractures inside the rock sample, and the average angle between the fracture surface of the fractures inside the rock sample and the direction of the maximum horizontal principal stress of the original in-situ stress field, in the background experiment. The remaining rock samples are then subjected to other fracturing schemes, such as synchronous fracturing or zipper fracturing. It should be noted that the fracturing method of the background experiment is the same as that of the simple fracturing described in the embodiment of this specification.

A step 507: calculating the stress field proactive utilization coefficient after the fracturing is completed;

this step specifically includes calculating the proactive utilization coefficient for fracturing the remaining rock samples according to the respective fracturing schemes by the formulas (1) to (4) of the present specification, after the fracturing is completed.

A step 508: quantitatively evaluating the effect of proactive utilization of the stress field under the fracturing scheme;

this step specifically includes quantitatively evaluating the effect of proactive utilization of the spatial stress field in the individual fracturing schemes according to the stress field proactive utilization coefficient and a preset proactive utilization coefficient threshold value.

Figure 6:
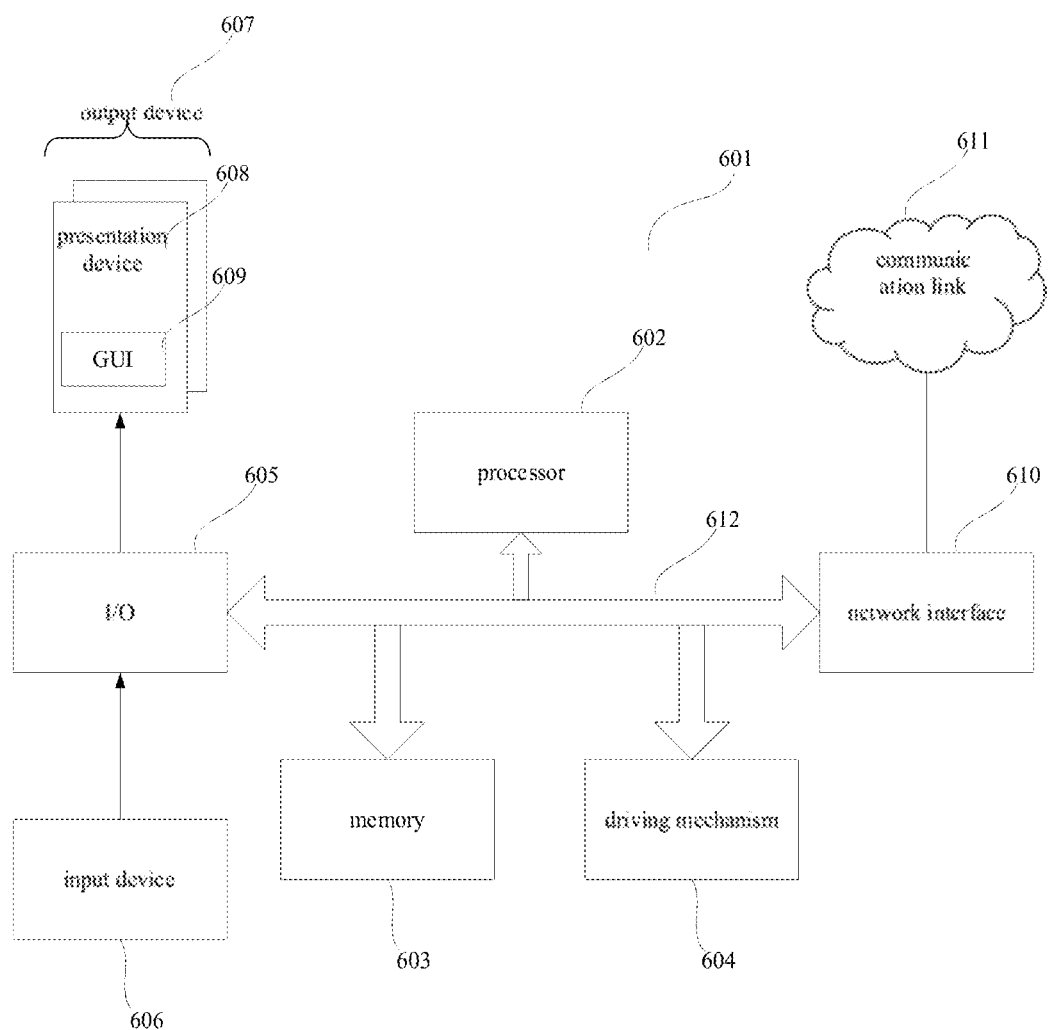
FIG. 6 is a structural schematic diagram of a computer device according to an embodiment of the present invention.

FIG. 6 is a structural schematic diagram of a computer device according to an embodiment of the present invention. The processing device 106 herein may be a computer device in this embodiment that performs the method herein described above. The computer device 601 may include one or more processors 602, such as one or more central processing units (CPUs), each of which may implement one or more hardware threads. The computer device 601 may also include any memory 603 for storing any kind of information, such as codes, settings, data, or the like. By way of non-limiting examples, the memory 603 may include any one or more of the following: any type of RAM, any type of ROM, a flash device, a hard disk, an optical disk, or the like. More generally, any memory may use any technique to store information. Further, any memory may provide a volatile or non-volatile retention of information. Further, any memory may represent a stationary or removable component of the computer device 601. In one case, when the processor 602 executes associated instructions stored in any memory or combination of the memories, the computer device 601 may perform any of the operations of the associated instructions. The computer device 601 also includes one or more driving mechanisms 604 for interacting with any memory, such as a hard disk driving mechanism, an optical disc driving mechanism or the like.

The computer device 601 may also include an input/output module 605 (I/O) for receiving various inputs (via the input device 606) and for providing various outputs (via the output device 607). One particular output mechanism may include a presentation device 608 and an associated graphical user interface (GUI) 609. In other embodiments, the input/output module 605 (I/O), the input device 606, and the output device 607 may also be excluded, as just one computer device in the network. The computer device 601 may also include one or more network interfaces 610 for exchanging data with other devices via one or more communication links 611. One or more communication buses 612 couple the components described above together.

The communication link 611 may be implemented in any manner, such as over a local area network, a wide area network (e.g., the Internet), a point-to-point connection, or the like, or any combination thereof. The communication link 611 may include any combination of hardwired links, wireless links, routers, gateway functions, name servers, etc., governed by any protocol or combination of protocols.

Corresponding to the method in FIGS. 3 to 5, the embodiment of the present disclosure further provides a computer readable storage medium which stores a computer program that, when run by a processor, executes the above steps.

The embodiment of the present disclosure further provides computer readable instructions, wherein when the instructions are executed by the processor, the program therein causes the processor to execute the method shown in FIGS. 3 to 5.

It is to be understood that in the various embodiments of the present disclosure, the serial numbers of the processes described above do not mean a sequential order of execution, the sequence in which the processes are executed should be determined in terms of the functions and inherent logic thereof, and should not constitute any limitation to the implementation process of the embodiment of the present disclosure.

It should also be understood that in the embodiment of the present disclosure, the term "and/or" is merely an association relationship that describes an associated object, meaning that three relationships may exist. For example, "A" and/or "B" may mean that "A" exists alone, and "A" and "B" exist together and "B" exists alone. In addition, the character "/" in the present disclosure generally indicates that the associated objects are in an "OR" relationship.

Those ordinarily skilled in the art can appreciate that the units and algorithm steps of the examples described in connection with the embodiments disclosed herein can be implemented in electronic hardware, computer software, or a combination of both. In order to clearly illustrate the interchangeability of hardware and software, the composition and steps of each example have been described in the above specification in a functional general manner. Whether these functions are performed in hardware or software depends on the specific disclosure and design constraints of the technical solution. The professionals may use different methods to implement the described functionality for each particular disclosure, but such implementations should not be considered beyond the scope of the present disclosure.

It will be apparent to those skilled in the art that for convenience and brevity of description, reference may be made to the corresponding procedures in the foregoing method embodiment for the specific operating procedures of the system, the device, and units described above, and the details are not repeated here.

What is claimed is:

1. A system for evaluating an effect of proactive utilization of a spatial stress field in laboratory, comprising:
    a rock sample placement device for placing a rock sample which is provided therein with a plurality of wellbores, the wellbores being provided with a plurality of perforations, the perforations in any adjacent two of the wellbores are staggered in horizontal and vertical directions of the rock sample;
    a confining pressure control device for applying a set confining pressure to the rock sample in the rock sample placement device to simulate an original in-situ stress field of the rock sample in an actual formation;
    a fracture imaging device for acquiring morphology and number of fractures inside the rock sample;
    a fracturing fluid injection device connected to one end of the wellbores of the rock sample, for injecting fracturing fluid into the perforations in the wellbores of the rock sample to form fractures within the rock sample;
    a stress measurement device for measuring stress values inside the rock sample while injecting the fracturing fluid into the perforations of the wellbores by the fracturing fluid injection device; and
    a processing device for calculating a stress field proactive utilization coefficient of the rock sample based on morphology of the fractures, the number of the fractures, and the stress values, and for quantitatively evaluating the effect of proactive utilization of the spatial stress field according to the stress field proactive utilization coefficient and a preset proactive utilization coefficient threshold value.

2. The system for evaluating the effect of proactive utilization of a spatial stress field in laboratory according to claim 1,
    wherein the perforation is provided with a valve, and the fracturing fluid injection device further comprises a fracturing fluid injection pump, a flow switching control unit, a wellbore pressure balancing unit, and a flow injection control unit;
    the fracturing fluid injection pump is connected to a first end of the flow switching control unit, a second end of the flow switching control unit is connected to head ends of all of the wellbores of the rock sample, and tail ends of all of the wellbores of the rock sample are connected to the wellbore pressure balancing unit, and the flow injection control unit is connected to the valve on the perforations;
    the fracturing fluid injection pump is used to inject the fracturing fluid into the head ends of all of the wellbores of the rock sample in a predetermined order though the control of the flow switching control unit;
    the flow switching control unit is used to control a flow rate of the fracturing fluid, a sequence of injection of the fracturing fluid injected into the wellbores of the rock sample;
    the flow injection control unit is used to control opening or closing of the valve on the perforations, thereby controlling the sequence of injection of the fracturing fluid injected into the perforations of the wellbore; and
    the wellbore pressure balancing unit is used to control communication of the tail ends of the wellbores of the rock sample so as to balance the pressure inside the wellbores of the rock sample.

3. The system for evaluating the effect of proactive utilization of a spatial stress field in laboratory according to claim 1,
    wherein the stress measurement device further comprises a plurality of stress sensors disposed inside the rock sample; and
    the stress sensors are used to measure stress values at individual points within the rock sample.

4. The system for evaluating the effect of proactive utilization of a spatial stress field in laboratory according to claim 1,
    wherein the rock sample placement device further comprises a water injection valve and a water discharge valve,
    wherein the water injection valve is connected to the fracturing fluid injection device;
    the fracturing fluid injection device is further used to inject the fracturing fluid into an interior of the rock sample placement device through the water injection valve so as to soak the rock sample in the fracturing fluid; and
    the water discharge valve is used to discharge the fracturing fluid from the interior of the rock sample placement device.

5. The system for evaluating the effect of proactive utilization of a spatial stress field in laboratory according to claim 4,
    wherein the system further comprises a vacuum pump, and the rock sample placement device further comprises a vacuum pump valve;
    the vacuum pump is located outside the rock sample placement device and is connected to the vacuum pump valve of the rock sample placement device; and
    the vacuum pump is used to pump gas from the interior of the rock sample placement device through the vacuum pump valve after a fluid level of the fracturing fluid is above an upper surface of the rock sample.

6. The system for evaluating the effect of proactive utilization of a spatial stress field in laboratory according to claim 1,
    wherein the system further comprises a temperature control device; and
    the temperature control device is used for regulating temperature inside the rock sample placement device.

7. A method for evaluating the effect of proactive utilization of a spatial stress field in laboratory that utilizes the system for evaluating the effect of proactive utilization of a spatial stress field in laboratory according to claim 1, comprising:
    placing the rock sample in the rock sample placement device;

applying a set confining pressure by the confining pressure control device to the rock sample in the rock sample placement device to form an original in-situ stress field of the rock sample in an actual formation;

injecting the fracturing fluid into perforations in the wellbores of the rock sample in the rock sample placement device by the fracturing fluid injection device in accordance with a fracturing scheme, so that the fractures are formed within the rock sample, and the fracturing scheme includes a start time at which the fracturing fluid is injected into each of the perforations and a flow curve over time for injecting the fracturing fluid into each of the perforations;

acquiring, by the fracture imaging device, morphology and number of fractures inside the rock sample;

measuring, by the stress measurement device, the stress values inside the rock sample;

calculating a stress field proactive utilization coefficient of the rock sample based on morphology of the fractures, the number of the fractures, and the stress values; and quantitatively evaluating the effect of proactive utilization of the spatial stress field according to the stress field proactive utilization coefficient and a preset proactive utilization coefficient threshold value.

8. The method for evaluating the effect of proactive utilization of a spatial stress field in laboratory according to claim 7, wherein the fracture morphology further comprises a fracture area and a tortuosity of the fracture;

a formula for calculating a stress field proactive utilization coefficient of the rock sample based on the morphology of the fractures and the stress values is:

$$Q_j = \frac{\frac{n_j}{\overline{\sigma}_j}\sum_{i=1}^{n_j}S_{i,j}\tau_{i,j}\sin\overline{\theta}_{i,j}}{\frac{n_1}{\overline{\sigma}_1}\sum_{i=1}^{n_1}S_{i,1}\tau_{i,1}\sin\overline{\theta}_{i,1}},$$

wherein $Q_j$ represents the stress field proactive utilization coefficient, which is calculated by the j-th experiment using an experimental method for evaluating the effect of proactive utilization of the spatial stress field in laboratory, $n_j$ represents the number of fractures created on the rock sample through the j experiments, $\overline{\sigma}_j$ represents an average value of the stress values obtained by measurement at a plurality of positions inside the rock sample by the stress measurement device after completion of the j-th experiment, $S_{i,j}$ represents the fracture area of the i-th fracture among the fractures generated in the rock sample after completion of the j-th experiment, $\tau_{i,j}$ represents the tortuosity of the i-th fracture among the fractures generated in the rock sample after completion of the j-th experiment, $\overline{\theta}_{i,j}$ represents an average angle between a fracture surface of the i-th fracture and a direction of the maximum horizontal principal stress of the original in-situ stress field, in the fractures generated in the rock sample after completion of the j-th experiment, j=1 represents a background experiment carried by the experimental method for evaluating the effect of proactive utilization of the spatial stress field in laboratory;

wherein the background experiment comprises:

a step S1: injecting, by the fracturing fluid injection device, the fracturing fluid into the plurality of perforations of the wellbore of the rock sample sequentially in a far-to-near order of distances from the perforations to the fracturing fluid injection device, according to the fracturing scheme of the background experiment; and a step S2: after completion of injection of the fracturing fluid into all of the perforations of the wellbore, repeating the step S1 in another wellbore until all perforations of all wellbores of the rock sample complete injection of the fracturing fluid to obtain the number $n_1$ of the fractures generated on the rock sample, the average value $\overline{\sigma}_1$ of the stress values at a plurality of locations inside the rock sample, the fracture area $S_{i,1}$ and the tortuosity $\sigma_{i,1}$ of the fractures inside the rock sample, and the average angle $\overline{\theta}_{i,1}$ between the fracture surface of the fractures inside the rock sample and the direction of the maximum horizontal principal stress of the original in-situ stress field, in the background experiment.

9. The method for evaluating the effect of proactive utilization of a spatial stress field in laboratory according to claim 8, wherein the step of calculating the average angle between the fracture surface of the fracture and the direction of the maximum horizontal principal stress of the original in-situ stress field includes:

dividing the fracture surface into N segments in a longitudinal direction of the rock sample to obtain N+1 horizontal planes, each horizontal plane intersecting the fracture surface of the fracture to form a fracture curve;

calculating angles between the fracture curves and the direction of the maximum horizontal principal stress of the original in-situ stress field, respectively; and calculating an average value of sum of the angles between the fracture curves and the direction of the maximum horizontal principal stress of the original in-situ stress field according to the number of the fracture curves, and taking the average value of the sum of the angles as the average angle between the fracture surface of the fractures and the direction of the maximum horizontal principal stress of the original in-situ stress field.

10. The method for evaluating the effect of proactive utilization of a spatial stress field in laboratory according to claim 9, wherein the step of calculating angles between the fracture curves and the direction of the maximum horizontal principal stress of the original in-situ stress field includes:

calculating the angle between the fracture curve and the direction of the maximum horizontal principal stress of the original in-situ stress field by the formula $$\overline{\theta} = \int_L \frac{1}{\rho(\theta)}ds = \int_{\theta\_start}^{\theta\_end}\frac{\sqrt{\rho^2(\theta)+\rho'^2(\theta)}}{\rho(\theta)}d\theta$$

in a polar coordinate system of the fracture curve, wherein $\overline{\theta}$ represents the angle between the fracture curve and the direction of the maximum horizontal principal stress of the original in-situ stress field, L represents a length of the fracture curve, $\rho(\theta)$ represents a representation of a path of the fracture curve in the polar coordinate system, $\theta$ represents an angular coordinate of any point on the path of the fracture curve in the polar coordinate system, $$\int_L \frac{1}{\rho(\theta)}ds$$

represents integration of the function ρ(θ) over the length of the fracture curve along an arc length derivative ds-curve, $$\rho'(\theta) = \frac{d\rho(\theta)}{d\theta}$$

and θ_start, θ_end represent the angular coordinates of a starting point and an ending point of the path of the fracture curve in the polar coordinate system, respectively; or, calculating the angle between the fracture curve and the direction of the maximum horizontal principal stress of the original in-situ stress field by the formula $$\bar{\theta} = \int_L f(s)ds = \int_{x\_start}^{x\_end} \frac{\sqrt{1+f'^2(x)}}{\sqrt{x^2+f^2(x)}} dx$$

in a plane rectangular coordinate system of the fracture curve, wherein $\bar{\theta}$ represents the angle between the fracture curve and the direction of the maximum horizontal principal stress of the original in-situ stress field, L represents the length of the fracture curve, $f(x)$ represents a representation of the path of the fracture curve in the plane rectangular coordinate system, x represents an abscissa of any point on the path of the fracture curve in the plane rectangular coordinate system, $\int_L f(s)ds$ represents integration of the function $f(x)$ over the length of the fracture curve along the arc length derivative ds-curve, $$f'(x) = \frac{df(x)}{dx}$$

and x_start, x_end represent an abscissa of a starting point and an ending point of the path of the fracture curve in the plane rectangular coordinate system, respectively; and any point on the path of the fracture curve satisfies $$\tan\theta_{uni} = f'(x) = \frac{\rho(\theta)\cos\theta + \rho'(\theta)\sin\theta}{-\rho(\theta)\sin\theta + \rho'(\theta)\cos\theta},$$

wherein $\theta_{uni}$ represents the direction of the maximum horizontal principal stress at a certain point on the path of the fracture curve.

* * * * *